United States Patent [19]

Wu et al.

[11] Patent Number: 5,294,230
[45] Date of Patent: Mar. 15, 1994

[54] METHOD FOR PERMANENT WAVING AND STRAIGHTENING OF HAIR

[75] Inventors: Maw-Sheng Wu, Lexington; Mary A. Pesce, Chestnut Hill, both of Mass.

[73] Assignee: The Gillette Company, Boston, Mass.

[21] Appl. No.: 831,822

[22] Filed: Feb. 6, 1992

Related U.S. Application Data

[63] Continuation of Ser. No. 336,252, Apr. 11, 1989, abandoned, which is a continuation of Ser. No. 65,329, Jun. 22, 1987, abandoned, which is a continuation-in-part of Ser. No. 36,588, Apr. 10, 1987, abandoned, which is a continuation-in-part of Ser. No. 884,774, Jul. 11, 1986, abandoned.

[51] Int. Cl.$^5$ .......................... A61K 7/06; A61K 7/09; A45D 7/04
[52] U.S. Cl. .................... 8/127.51; 132/203; 132/204; 132/209; 424/71; 424/72
[58] Field of Search ............... 8/127.51, 127.6; 132/7, 132/203, 204, 206, 209; 424/71, 72

[56] References Cited

U.S. PATENT DOCUMENTS

| | | | |
|---|---|---|---|
| 3,017,328 | 1/1962 | Childrey | 427/47 |
| 3,644,084 | 2/1972 | Hsiung | 427/47 |
| 3,981,987 | 9/1976 | Linke | 8/127.51 |
| 4,214,596 | 7/1980 | Kaplan | 424/70 |
| 4,322,401 | 3/9182 | Harada | 424/70 |
| 4,494,557 | 1/1985 | Nagel | 132/7 |
| 4,504,466 | 3/1985 | Eda | 424/72 |
| 4,602,648 | 7/1986 | Syed | 132/7 |
| 5,041,286 | 8/1991 | Donnelly et al. | 424/71 |
| 5,071,641 | 12/1991 | Lewis | 424/71 |
| 5,165,427 | 11/1992 | Borish | 132/204 |
| 5,223,252 | 6/1993 | Kolc et al. | 424/72 |

FOREIGN PATENT DOCUMENTS

| | | |
|---|---|---|
| 958501 | 2/1957 | Fed. Rep. of Germany . |
| 1959149 | 5/1970 | Fed. Rep. of Germany . |
| 780037 | 7/1957 | United Kingdom . |
| 1119845 | 7/1968 | United Kingdom . |
| 1125794 | 8/1968 | United Kingdom . |
| 2066310 | 7/1981 | United Kingdom . |

Primary Examiner—Prince Willis, Jr.
Assistant Examiner—J. Silbermann
Attorney, Agent, or Firm—Stephan P. Williams; Mandel E. Slater

[57] ABSTRACT

Hair is waved or straightened by maintaining it in tightly curled or in straightened configuration in contact with an aqueous waving lotion containing sulfite, bisulfite, or hydrosulfite together with a water-soluble mercaptan, at a molar ratio of 5:1 to 1:7.5, rebuilding with an aqueous lotion at pH 7 to 12 free from crosslinking, oxidizing, or reducing agents, and subsequently applying a neutralizer solution. Minimal damage to the hair results from use of the specified molar ratio. When waving hair, an optional additional step between crosslinking and neutralizing comprises maintaining the rebuilt hair in stress-free condition in contact with the ambient atmosphere to permit the curled hair to relax to the desired extent.

13 Claims, No Drawings

METHOD FOR PERMANENT WAVING AND STRAIGHTENING OF HAIR

This is a continuation of copending application Ser. No. 07/336,252 filed on Apr. 11, 1989 now abandoned, which is a continuation of U.S. Ser. No. 07/065,329, filed Jun. 22, 1987 (now abandoned), which is a continuation-in-part of U.S. Ser. No. 07/036,588, filed Apr. 10, 1987 (now abandoned), which is a continuation-in-part of U.S. Ser. No 06/884,774, filed Jul. 11, 1986 (now abandoned).

This invention relates to cold permanent or temporary waving or straightening of hair and pertains more specifically to a composition and method for controlling tightness and durability of a wave, and for providing waved or straightened hair having very low damage. By "cold permanent" waving or straightening is meant production of an enduring wave or curl in the hair, or straightening of the hair, at a temperature below about 50° C., with or without the external application of heat to the hair, as distinguished from hot permanent waving or straightening in which the hair is heated to elevated temperatures of the order of 90° C. By "temporary" waving is meant production of a wave which gradually relaxes and which is substantially completely lost within a few weeks at most under ordinary conditions, a result desired by those who wish to change their styles frequently. By cold "straightening" is meant removal of curls or kinks from hair at a temperature below about 50° C. without the need for use of a heated comb or other heated implement. By "damage" is meant embrittlement and weakening of the hair as shown by increased breakage under stress, and increase in susceptibility to further damage when subsequently dyed, bleached or again waved. It is proportional to the number of unreformed keratin disulfide bonds in the hair after waving.

It has previously been proposed in Hsiung et al., U.S. Pat. No. 3,644,084 to wave hair by curling it while softened by sulfitolysis, but significant damage to the hair as measured by a decrease in modulus ranging from 21% to 49% was reported. Moreover, neither the method of this patent nor other procedures for cold permanent waving hair provide any means for adjusting or controlling the extent of the wave without previous experience with the particular hair being waved. Since the susceptibility of human hair to permanent waving varies from individual to individual, it has been common practice, when an individual head of hair is being waved for the first time with a particular waving composition or procedure, to subject a small test tress of the hair to the procedure under conventional conditions of winding, time of treatment, concentration of waving lotion and of neutralizer, in order to determine results, then adjust the conditions of waving the hair on the head to bring the expected results as close as possible to those desired by the individual receiving the wave. Once the wave has been completed, it can be varied in tightness only by repeating the entire process.

It has now been found that remarkably low damage to the hair can be achieved by using for curling or straightening (removing the kinks from) hair an aqueous lotion containing in combination with a sulfite (or bisulfite or hydrosulfite) a water-soluble mercaptan such as cysteine or the like in the range of molar proportions from 5:1 to 1:7.5 sulfite:mercaptan and in concentration ranges of sulfite from 0.1 to 1.5 molar and of mercaptan from 0.1 to 1.5 molar, at pH 5.5 to 8.5, preferably 6.5 to 7.5, followed by rebuilding the hair by applying an aqueous rebuilding lotion at pH 7 to 12, free from cross linking agents, oxidizing agents, and reducing agents. The resulting temporary wave or straightening of the hair can be rendered permanent at any desired subsequent time by applying an aqueous neutralizer lotion containing an oxidizing agent to set the hair in the desired configuration. In the case where hair is to be curled or waved, it is possible to loosen the tightness of the curl or wave, if desired, simply by adding a step between the rebuilding step and the neutralizing step, the added step comprising maintaining the curled and rebuilt hair exposed to air in stress-free condition at ambient temperature for a time sufficient to cause the hair to relax to a less tightly curled configuration. In practice, it is found that this relaxing step requires at least eight hours, preferably sixteen or more, to bring about significant relaxation. This makes it possible for the individual receiving the wave or for the operator administering it to control the tightness of the wave by inspecting it at intervals during the relaxation period and rendering it permanent, that is, nearly stopping or at least slowing to a much greater extent the further relaxation at any desired point simply by applying a conventional neutralizer lotion. Analogous results are achieved in straightening hair by the present invention.

The very low level of damage to the hair makes it possible to color the hair on the same day that it is waved.

The foregoing also makes possible an improved process in which the hair is first wet only with water, not with waving lotion, before wrapping on curlers. The waving lotion is then applied to all of the wrapped tresses simultaneously, assuring uniform results, particularly in the case of strong waves. The extent of damage can readily be measured by methylene blue absorption as described in U.K. Patent GB 2,027,195B, or by measuring relative modulus of the hair before treating and of the hair after treatment, the measurement described in Hsiung U.S. Pat. No. 3,644,048.

Consequently, the invention comprises a method of waving or straightening human hair which comprises maintaining the hair in curled or straightened configuration and in contact with a first aqueous lotion containing a water-soluble mercaptan together with a water-soluble sulfite, bisulfite or hydrosulfite at pH 5.5 to 8.5, to impart a change in configuration to the hair, rebuilding the hair by contacting it with an aqueous lotion at pH 7 to 12 free from cross-linking agents, oxidizing agents, or reducing agents, and, if permanency is desired, applying to said rebuilt hair an aqueous lotion containing an oxidizing neutralizing agent to set the hair in the desired configuration. If a somewhat higher curl or wave level in the hair is desired, it is preferred to employ a rebuilding lotion hving a pH from 8.5 to 12, or most desirably a pH from 9 to 11. Tap water at a pH of approximately 7 is the most convenient rebuilding lotion for home use. Optionally, the process comprises waving hair by the foregoing process including the additional step after rebuilding and before neutralizing, of maintaining the hair free from stress exposed to air at ambient temperature for a time sufficient to cause said curled and rebuilt hair to relax to a less tightly curled condition.

The waving or straightening lotion containing a water soluble mercaptan together with a sulfite, bisulfite or hydrosulfite serves to soften the hair fibers and render them plastic so that they can assume the desired configuration. In the practice of the invention, the hair to be waved is wound on curlers in the usual manner, the curler mandrel preferably having a diameter from 0.15 to 4 cm, and is maintained in the curled configuration while in contact with the waving lotion and during the rebuilding step. If desired, the hair may be covered with a turban during either or both of the waving and rebuilding steps, and it may be rinsed, e.g. with water, after the rebuilding step, although rinsing is not essential, particularly when water alone is used as the aqueous rebuilding lotion. If the hair is subjected to the optional relaxing step after rebuilding, it is first unwound or removed from the curlers so as to be free from stress during this step, then rewound on curlers for the sake of convenience, although rewinding is not absolutely essential, before application of the oxidizing or neutralizing agent. If the optional relaxing step is omitted, the hair is simply allowed to remain on the curlers until after application of the oxidizing or neutralizing agent. In both cases, following application of the oxidizing or neutralizing agent to render the wave or straightening permanent, there may be a final water rinse.

In practicing the invention to straighten hair, the straightening lotion containing water-soluble mercaptan and sulfite, bisulfite or hydrosulfite is preferably thickened with any conventional thickening agent inert to the lotion and to the hair such as a gum, e.g. guar gum or a derivative thereof or other natural, water-soluble gum or a hydrocolloid, e.g. carrageenan or agar or other water-soluble polysaccharide, polyvinyl alcohol or a vinyl polymer with carboxyl groups, e.g. Carbopol, fumed silica, etc., so that the lotion will not run or drip off the hair; the thickened lotion is then combed repeatedly through the hair so as to apply straightening tension or stress to the hair until the desired degree of straightness is achieved. The aqueous lotion applied during the rebuilding step after straightening may likewise be thickened and applied by combing, although this is not essential provided the hair is maintained in straightened configuration during the rebuilding step. Rinsing with water may follow the straightening step and/or the rebuilding step if desired, although water alone may be used as the aqueous rebuilding lotion.

It is also possible in some cases to combine waving and straightening (i.e. de-kinking) of hair by wrapping the hair on curlers under sufficient tension to remove kinks and maintaining it under tension while the waving or straightening lotion and the rebuilding lotion are applied.

The waving or straightening lotion may contain any water-soluble sulfite, bisulfite or hydrosulfite, such as an alkali metal or ammonium or alkanolamine salt of the appropriate acid. The relative proportions of sulfite, bisulfite and hydrosulfite depend on the pH of the solution, which may vary from 5.5 to 8.5, but is preferably about 6.5 to 7.5. Of the alkanolamine salts the trialkanolamine salts are preferred; it is preferred to avoid monoalkanolamine salts because of smell and tendency to act as a cross-linking agent. Conventional alkaline materials or alkaline buffers such as alkali metal or ammonium hydroxide or the trialkanolamines may be used to adjust the pH, or the corresponding carbonates or bicarbonates may be used in place of the hydroxides. The concentration of the sulfite, bisulfite or hydrosulfite in the waving lotion may vary from 0.1 to 1.5 molar provided the molar proportion of sulfite to mercaptan remains within the range specified.

The water-soluble mercaptan present in the waving lotion is preferably cysteine, but a variety of mercaptans can be used, preferably aliphatic mercaptans such as thioglycolic acid. dimercapto adipic acid, thiolactic acid, their salts and alkyl esters, thioglycol, thioglycerol or the like. The mercaptan may be present in an amount from 0.1 molar to 1.5 molar. For ensuring minimal damage to the hair, not only must the concentrations be within the foregoing limits, but the molar ratio of total sulfite, that is, of sulfite, bisulfite and/or hydrosulfite to mercaptan must be from 5:1 to 1:7.5, preferably 2.5:1 to 1:2.5.

The waving or straightening lotion (sulfitolzying solution) can be provided to the consumer in the form of a single ready to-use solution in the case of those mercaptans which are stable in solution, such as thioglycolic acid, dimercapto adipic acid, thiolactic acid, and their salts and alkyl esters, thioglycol and thioglycerol. However, the preferred mercaptan cysteine is unstable in such a solution so that the complete solution must be prepared by the user shortly before it is used. Consequently, the preferred embodiment of the invention is supplied to the consumer in the form of a kit comprising one container having a specific quantity of an aqueous lotion containing in solution water-soluble sulfite, bisulfite or hydrosulfite, such as an alkali metal, ammonium or alkanolamine salt of the appropriate acid at a concentration of 0.1 to 1.5 molar, and at a pH from 5.5 to 8.5, preferably about 6.5 to 7.5. A buffer to adjust pH is optional. The kit also comprises a second container of cysteine in dry solid form, with directions to dissolve the cysteine in the aqueous sulfitolyzing solution before use. The amounts of ingredients in the kit should be such that the molar ratios and concentrations are in the desired ranges as set forth above. In the embodiments of the invention having mercaptans other than cysteine, it is also possible, if desired, to supply the consumer with a kit having the waving or straightening lotion in one container and the mercaptan in a separate container, either in pure form or in aqueous solution.

It is also desirable but not essential that the waving or straightening lotion contain a wetting agent, preferably a non ionic wetting agent such as polyoxyethylene lauryl ether, polyoxyethylene monostearate, polyoxyethylene alkyl phenol, sorbitan monolaurate, or the like. Anionic wetting agents can also be used such as triethanolamine oleate, sodium lauryl sulfate, sodium stearate and the like. Swelling agents such as alcohol or urea or dimethyl urea or lactams may also be present. In addition, there may be present in the waving or straightening lotion a conventional hair conditioning agent such as a quaternary ammonium salt containing a long-chain aliphatic group. Among representative hair conditioning agents are N-alkyl trimethyl ammonium chloride in which the alkyl group contains 10–20 carbon atoms, soya trimethyl ammonium chloride, di-soya dimethyl ammonium chloride, di coco dimethyl ammonium chloride, polymethacrylamidopropyl trimethyl ammonium chloride, quaternium-15, cetyl dimethyl hydroxyethyl ammonium chloride, quaternium-40, and the like. Wetting agents and hair conditioning agents and swelling agents when present are in amounts generally considered effective for their intended purpose, of the order of 0.01 to 1% by weight for the first two, and larger amounts, of the order of 3–20% by weight, of swelling agents. Conventional additives such as emollients, coloring agents, fragrances, preservatives, etc. may also be present.

These optional agents may be supplied in one or more separate containers in the kit, or they may be combined with the waving lotion in ready to use form. In the case of the preferred mercaptan cysteine, the optional agents are preferably combined with the aqueous sulfite, bisulfite or hydrosulfite solution.

The hair is maintained in contact with the waving or straightening lotion, preferably at ambient temperature, for a sufficient time, usually 5 to 60 minutes, to soften the hair to a plastic condition enabling it to assume its tightly wound configuration or straightened (dekinked) configuration with little or no tendency to revert to its original configuration. A plastic turban or other cover for the hair may be employed during this stage to accelerate the process, or the hair can be gently warmed, if desired.

The aqueous lotion employed for the rebuilding step to restore many of the disulfide linkages in the hair keratin can be water alone, having a pH of about 7, but for somewhat higher curl levels the pH of the aqueous rebuilding lotion should be higher, preferably containing an alkaline agent such as ammonium hydroxide or an alkaline metal carbonate or bicarbonate or a trialkanolamine to adjust the pH to a level from 8.5 to 12.0 or to the most preferred level of 9.0 to 11. The aqueous rebuilding lotion may optionally contain a conventional wetting agent and/or hair conditioning agent, emollient, coloring agent, fragrance, preservative, etc. If the hair conditioning agent or wetting agent is present in the waving lotion, the effective concentration of those agents in the aqueous rinse can be lower than in the waving lotion, of the order of 0.005 to 0.1% by weight. It is also essential that the aqueous lotion be free from cross-linking, oxidizing, or reducing agents in order to achieve the benefits of the present invention, and that it be applied to the hair while the latter is still in wound or straightened configuration. Cross-linking agents which must be excluded from the aqueous rebuilding lotion include such reagents as aldehydes, ketones, low molecular weight amines such as monoethanol amine and alkyl amines containing 1 to 6 carbon atoms, polyvalent metal salts, and like reagents reactive with thio or mercapto groups of the treated hair. Oxidizing agents which must be excluded include hydrogen peroxide, sodium bromate, sodium perborate, and other conventional oxidizing neutralizers. Reducing agents which must be excluded include various mercaptans such as any of those present in the waving or straightening lotion, sodium borohydride, and other reducing agents capable of reducing disulfide groups of the hair.

In sulfite waving or straightening of the hair, the reaction between the disulfide linkages in the hair keratin and the sulfite leads to breakage of the disulfide bond and the formation of both S-sulfo groups and mercapto (or thio) groups on the hair keratin, as represented in the following equation:

In the process of the present invention, in which both sulfite and mercaptan are present within the specified range of proportions, it is believed that the reaction produces essentially no keratin-S-sulfo groups, the sulfite acting essentially as a catalyst; instead, there are produced a mixed disulfide and a keratin mercaptan in accordance with the following equation:

In the second step of the present invention, the rebuilding step it is believed that the excess aqueous rebuilding lotion lowers the concentration of water-soluble mercaptan by dilution; this, together with the optional increase in pH shifts the equilibrium of the last reaction to the left and restores in part the disulfide linkages of the keratin in the new configuration of the hair. When a conventional neutralizer solution containing an oxidizing agent is subsequently applied to the hair, the soluble mercaptan is completely destroyed by oxidation and is removed from the hair along with any residual sulfite, thus ensuring permanence of the new configuration of the hair.

When the invention is supplied to consumers in the form of a kit, the aqueous rebuilding lotion may be supplied in an individual container in appropriate quantity. If it is water alone, it may ordinarily be omitted from the kit.

Ordinarily, the step of rebuilding by maintaining the wound hair in contact with the aqueous rebuilding lotion requires from 1 to 50 minutes at ambient temperature. If desired, a turban may be used and/or the hair may be gently heated to a temperature as high as 50° C.

In the case where ammonium sulfite, bisulfite or hydrosulfite is employed in the waving or straightening lotion, it is desirable but not essential to carry out the rebuilding in two steps, first by rinsing with tap water at pH 5 to 7 to remove ammonium salts, then by applying rebuilding lotion at pH 7 to 12. The tap water rinse avoids the formation of free ammonia with its attendant odor when the alkaline rebuilding lotion is applied; it may also serve as the rebuilding lotion itself, as pointed out above.

Following the aqueous rebuilding step, the hair, or a representative sample tress, may be removed from the curling rod and dried, if desired, in order to observe the tightness of the wave or the straightness of the hair. If the tightness or straightness is acceptable, the entire head of hair may then be saturated with a conventional neutralizing solution, that is, an aqueous solution of oxidizing agents such as peroxide, bromate, perborate, percarbonate or the like to set the hair permanently in its then curled or straightened configuration and to prevent any substantial further change in configuration, the effect of the neutralizing solution being to eliminate any residual mercaptan or sulfite in the hair.

In many cases of waving hair, however, it will be found that the initial curl imparted to the hair after the rebuilding step is tighter than is desired; in such case, the treatment with neutralizer is delayed, the hair after removal from the curlers being permitted to stand exposed to the atmosphere, wet or dry, under ambient conditions and free from stress so that it relaxes slowly to a less tightly wound condition because the rebuilding of the keratin disulfide has not been completed. When the relaxation has progressed to the desired extent, which may require only a few hours or as much as three weeks, usually from 8 to 48 hours, the curl or wave is rendered permanent and further relaxation is substantially prevented by application of the neutralizer solution in the usual manner. The relaxation occurs at a decreasing rate under ambient conditions; the curl or wave becomes completely lost in a few weeks. If desired, the rate of relaxation can be increased somewhat by raising the temperature.

When the invention is supplied in the form of a kit, the neutralizing solution may be packaged in appropriate quantity in an individual separate container.

The following examples will serve to illustrate more fully the nature of the present invention without acting as a limitation upon its scope.

EXAMPLE 1

The following waving lotion was prepared by mixing the specified ingredients together at room temperature.

| Ingredient | Percent By Weight |
| --- | --- |
| Ammonium Bisulfite | 6.38 (0.64 molar) |
| Cysteine | 4.76 (0.39 molar) |
| SD-40 denatured alcohol | 4.22 |
| Laureth 23 | 0.54 |
| Polymethacrylamidopropyl trimethylammonium chloride | 0.46 |
| Soya trimethylammonium chloride | 0.20 |
| Deionized water | q.s. to 100 |

The Laureth 23 functioned as a nonionic wetting agent and the quaternary compounds served as conditioning agents for the hair. When an optional additive of low solubility, such as a fragrance, is present, the amount of the Laureth 23 may be increased as necessary to facilitate dispersion. The pH of the solution was adjusted to 7.4–7.6 by the addition of ammonium hydroxide, whereupon about half of the ammonium bisulfite is converted to ammonium sulfite. The molar ratio of total sulfite and bisulfite to cysteine was 1.63:1.

The head of hair to be waved was shampooed, and rolled upon curlers having a mandrel diameter of 0.25 inch, then saturated with the foregoing waving solution, covered with a plastic turban, and allowed to stand for 40 minutes.

The turban was then removed and the hair was rinsed for two minutes with tap water, then towel-blotted dry. Thereupon an aqueous rebuilding lotion having the following composition (pH 10) was used to saturate the wound hair tresses:

| Ingredient | Percent By Weight |
| --- | --- |
| Sodium carbonate | 7.95 |
| Sodium bicarbonate | 2.1 |
| Quaternium-15 | 0.02 |
| Deionized water | q.s. to 100 |

Depending upon the source and purity of the ingredients, small adjustments of the amounts of the foregoing ingredients may be needed to achieve the desired pH of 10. The hair was covered with a turban, allowed to stand for 20 minutes. The turban can be omitted with substantially the same results. A sample tress was then removed from the curler and examined for tightness of wave. In one case, the recipient decided that the tightness of the wave was satisfactory and so, after a tap water rinse, the neutralizing solution was applied to the hair and allowed to stand for a few minutes. In another case, the recipient decided that the wave should be allowed to relax further, and so the hair was rinsed with tap water and allowed to dry, and the neutralizing solution was applied to the hair only after 48 hours. In both cases, the same neutralizing solution was employed, having the following composition:

| Ingredient | Percent By Weight |
| --- | --- |
| Hydrogen peroxide | 2.3 |
| Hydroxyethyl cetyl dimethyl ammonium phosphate | 1.25 |
| Quaternium-40 | 0.05 |
| Deionized water | q.s. to 100 |

The solution was adjusted to pH 3.0 by the addition of phosphoric acid and allowed to remain on the hair for approximately three minutes.

In both cases, the hair was rinsed with tap water alone following application of the neutralizing solution in order to eliminate reagents from the hair.

In order to determine the extent of damage to the hair a sample of a specimen of European hair was immersed in water for one hour at 30° C., then stretched by 1 percent of its length, and the modulus or force required to produce an additional 0.2% stretch was measured. An additional sample of the same specimen was subjected to the foregoing process, the neutralizing solution being applied immediately after the rebuilding step and the water rinse, with no intervening relaxation step. The treated hair, after final water rinse, was immersed in water at room temperature and its modulus determined using the same procedure as for the first sample. Each measurement was repeated two additional times. The average modulus of the treated hair was found to be 92.5% relative to the modulus of the original untreated hair.

Similar results are obtained by a neutralizing solution having the following composition:

| Ingredient | Percent By Weight |
| --- | --- |
| Hydrogen peroxide | 2.3 |
| Steartrimonium chloride | 2.5 |
| Polyquaternium-6 | 0.1 |
| Nonoxynol-9 | 2.0 |
| Phosphoric acid | 0.022 |
| Deionized water | q.s. to 100 |

Hair straightening can be accomplished by thickening the foregoing compositions by the addition of 1.5% by weight of guar hydroxypropyltrimonium chloride; the lotions are applied to the hair by combing; the procedure is otherwise the same as described above.

EXAMPLE 2

A waving lotion was prepared which was identical to that of Example 1 except that the concentration of ammonium bisulfite was 6.67% (0.67 molar), and that of cysteine was 1.19% (0.molar) to provide a molar ratio of total sulfite to mercaptan of 6.68:1. A specimen of European hair was then treated with this lotion following a procedure otherwise the same as in Example 1 (omitting the relaxing step). The relative modulus of the treated hair was 88% of the untreated hair.

EXAMPLE 3

An aqueous waving lotion was prepared having the following composition:

| Ingredient |
| --- |
| Ammonium bisulfite, 0.1 molar |
| Cysteine, 0.5 molar |
| SD-40 denatured alcohol, 5% by weight |
| Octyl phenoxy polyethoxy (9-10) |

-continued

| Ingredient |
| --- |
| ethanol (Triton X-100), 0.01% by weight |

The pH of the lotion was adjusted to 7.0 by addition of ammonium hydroxide. The molar ratio of total sulfite:-mercaptan was 1:5.

A specimen of hair was treated with this waving lotion following a procedure otherwise identical to that of Example 1 (omitting the relaxing step). The relative modulus of the treated hair was 99% of that of the untreated hair.

EXAMPLE 4

Results similar to those described above were obtained using a waving lotion having the following composition:

| Ingredient | Percent By Weight |
| --- | --- |
| Ammonium thioglycolate | 4.23 (0.39 molar) |
| Ammonium bisulfite | 4.76 (0.48 molar) |
| SD-40 denatured alcohol | 6 |
| Deionized water | q.s. to 100 | pH adjusted to 7.0 using ammonium hydroxide The mol ratio of bisulfite to thioglycolate was 1.24:1. Results were similar to those in Example 1.

EXAMPLE 5

In the procedures of Examples 1 and 4, there can be substituted for the rebuilding lotion the following composition:

| Ingredient | Percent By Weight |
| --- | --- |
| Glycine | 2.35 |
| Sodium chloride | 1.83 |
| Sodium hydroxide* | 0.6 |
| Isoceteth-20 | 0.25 |
| Quaternium-15 | 0.02 |
| Deionized water | q.s. to 100 |

*to adjust pH to 10

Results were similar to those obtained in the preceding Examples.

EXAMPLE 6

A waving lotion was prepared having the following composition in parts by weight:

| Ingredient | Percent By Weight |
| --- | --- |
| Ammonium bisulfite | 6.67 |
| SD-40 denatured alcohol | 4.43 |
| Isoceteth-20 | 2.25 |
| Fragrance | 0.75 |
| Laureth-23 | 0.57 |
| Polymethacrylamidopropyltrimonium chlor | 0.48 |
| Soytrimonium chloride | 0.21 |
| Isopropyl alcohol | 0.15 |
| Ammonia to pH 7.4–7.6 | |
| Deionized water | q.s. to 100 |

Into the foregoing mixture was dissolved 5 parts by weight of L-cysteine.

The lotion was applied to a head of hair as described in Example 1, after which the turban was removed, the hair was rinsed with water for a few minutes, and towel-blotted dry. The result was hair having a temporary wave, one which will disappear in about two weeks. To render it permanent, there may be applied to the hair a neutralizing lotion as described in Example 1, the neutralizing lotion being applied either immediately after the step of rebuilding with a water rinse or after a relaxation step as described above. In each case, the hair suffered very little damage, similar to the hair of Example 1.

What is claimed is:

1. The method of waving or straightening human hair consisting essentially of maintaining the hair in curled or straightened configuration and in contact with a first aqueous lotion at pH 5.5 to 7.5 containing dissolved therein a water-soluble mercaptan at a concentration from 0.1 to 1.5 molar together with a member of the group consisting of water soluble sulfite, bisulfite or hydrosulfite at a concentration from 0.1 to 1.5 molar, to impart a curled or straightened configuration to the hair, the molar ratio of said member to said mercaptan being 2.5:1 to 1:2.5 and rebuilding the curled or straightened hair by applying to it an aqueous rebuilding lotion at pH 7 to 12 comprising water or water containing an alkaline agent selected from the group consisting of ammonium hydroxide, alkali metal carbonates or bicarbonates, trialkanolamines, and mixtures thereof, said aqueous rebuilding lotion being free from crosslinking, oxidizing or reducing agents.

2. The method of claim 1 including the additional step of applying to said rebuilt curled or straightened hair an aqueous neutralizer lotion containing an oxidizing agent to neutralize and set the hair in permanently curled or straightened configuration.

3. The method of claim 1 in which said mercaptan is cysteine.

4. The method of claim 1, 2 or 3 in which the hair is waved, the pH of said first aqueous lotion is 6.5 to 7.5 and the pH of said aqueous rebuilding lotion is approximately 7.

5. The method of claim 1, 2 or 3 in which the hair is waved, the pH of said first aqueous lotion is 6.5 to 7.5 and the pH of said aqueous rebuilding lotion is 8.5 to 12.

6. The method of claim 1, 2, or 3 in which said sulfite, bisulfite or hydrosulfite is an ammonium salt and said hair is waved.

7. The method of claim 1, 2 or 3 in which said hair is waved, said method including the step, following rebuilding and before neutralizing, of maintaining the hair free from stress exposed to air at ambient temperature for a time sufficient to cause said curled and rebuilt hair to relax to a less tightly curled condition.

8. The method of claim 2 in which said hair is waved, said waving lotion contains cysteine as said mercaptan and said sulfite, bisulfite or hydrosulfite is an ammonium salt, the pH of said waving lotion is 6.5 to 7.5, and the pH of said rebuilding lotion is approximately 7.

9. The method of claim 8, said method including the step, following rebuilding and before neutralizing, of maintaining the hair free from stress exposed to air at ambient temperature for a time sufficient to cause said curled and rebuilt hair to relax to a less tightly curled condition.

10. The method of claim 2 in which said hair is waved, said waving lotion contains cysteine as said mercaptan and said sulfite, bisulfite or hydrosulfite is an ammonium salt, the pH of said waving lotion is 6.5 to 7.5, and the pH of said rebuilding lotion is 8.5 to 12.

11. The method of claim 9, said method including the step, following rebuilding and before neutralizing, of maintaining the hair free from stress exposed to air at ambient temperature for a time sufficient to cause said curled and rebuilt hair to relax to a less tightly curled condition.

12. The method of claim 1 wherein said mercaptan in said lotion is cysteine at a concentration of about 0.4 molar, said member in said lotion is at a concentration of about 0.7 molar, and the pH of said lotion is about 7.5.

13. The method of claim 12 wherein said member is ammonium bisulfite.

* * * * *